(12) United States Patent
Fradette et al.

(10) Patent No.: US 8,722,391 B2
(45) Date of Patent: May 13, 2014

(54) PROCESS FOR $CO_2$ CAPTURE USING CARBONATES AND BIOCATALYSTS WITH ABSORPTION OF $CO_2$ AND DESORPTION OF ION-RICH SOLUTION

(75) Inventors: Sylvie Fradette, Pintendre (CA); Julie Gingras, Quebec (CA); Jonathan Carley, Calgary (CA); Glenn R. Kelly, Trois-Rivieres (CA); Olivera Ceperkovic, Quebec (CA)

(73) Assignee: CO2 Solutions Inc., Quebec (CA)

( * ) Notice: Subject to any disclaimer, the term of this patent is extended or adjusted under 35 U.S.C. 154(b) by 0 days.

(21) Appl. No.: 13/388,871

(22) PCT Filed: Aug. 4, 2010

(86) PCT No.: PCT/CA2010/001214
§ 371 (c)(1),
(2), (4) Date: Feb. 3, 2012

(87) PCT Pub. No.: WO2011/014957
PCT Pub. Date: Feb. 10, 2011

(65) Prior Publication Data
US 2012/0129246 A1   May 24, 2012

Related U.S. Application Data

(60) Provisional application No. 61/231,037, filed on Aug. 4, 2009.

(51) Int. Cl.
*B01D 53/62* (2006.01)

(52) U.S. Cl.
USPC .......................................... 435/266; 252/190

(58) Field of Classification Search
USPC ....................................................... 435/266
See application file for complete search history.

(56) References Cited

U.S. PATENT DOCUMENTS

| | | | | |
|---|---|---|---|---|
| 7,132,090 | B2 * | 11/2006 | Dziedzic et al. | 423/230 |
| 7,998,714 | B2 * | 8/2011 | Gellett et al. | 435/168 |
| 2003/0143719 | A1 * | 7/2003 | Dutil et al. | 435/264 |
| 2008/0098892 | A1 | 5/2008 | Asprion et al. | |
| 2008/0159937 | A1 | 7/2008 | Ouimet | |
| 2010/0011956 | A1 * | 1/2010 | Neumann et al. | 95/151 |
| 2010/0092359 | A1 * | 4/2010 | Svendsen et al. | 423/230 |
| 2010/0300894 | A1 | 12/2010 | Lin et al. | |
| 2011/0182779 | A1 * | 7/2011 | Kawatra et al. | 422/187 |
| 2012/0009646 | A1 * | 1/2012 | Novick et al. | 435/188 |
| 2012/0009652 | A1 * | 1/2012 | Alvizo | 435/232 |

FOREIGN PATENT DOCUMENTS

| | | | |
|---|---|---|---|
| CA | 2 417 483 A1 | | 7/2003 |
| GB | 1 306 853 | | 2/1973 |
| WO | WO 2004/007058 | * | 1/2004 |
| WO | WO 2006/089423 A1 | | 8/2006 |
| WO | 2006/108532 A1 | | 10/2006 |
| WO | WO 2008/072979 | * | 6/2008 |
| WO | WO 2008/072979 A1 | | 6/2008 |
| WO | 2009/000025 A1 | | 12/2008 |
| WO | 2010/037109 A1 | | 4/2010 |
| WO | 2011/054107 A1 | | 5/2011 |

OTHER PUBLICATIONS

PCT International Search Report and Written Opinion for PCT/CA2010/001214, dated Nov. 5, 2010.
PCT International Search Report for PCT/CA2011/001210, dated Jan. 30, 2012.

* cited by examiner

*Primary Examiner* — Ralph Gitomer
(74) *Attorney, Agent, or Firm* — Dority & Manning, P.A.

(57) ABSTRACT

A formulation and process for capturing $CO_2$ use an absorption mixture containing water, biocatalysts and a carbonate compound. The process includes contacting a $CO_2$-containing gas with the absorption mixture to enable dissolution and transformation of $CO_2$ into bicarbonate and hydrogen ions, thereby producing a $CO_2$-depleted gas and an ion-rich solution, followed by subjecting the ion-rich solution to desorption. The biocatalyst improves absorption of the mixture comprising carbonate compounds and the carbonate compound promotes release of the bicarbonate ions from the ion-rich solution during desorption, producing a $CO_2$ gas stream and an ion-depleted solution.

20 Claims, 8 Drawing Sheets

PROCESS FOR CO₂ CAPTURE USING CARBONATES AND BIOCATALYSTS WITH ABSORPTION OF CO₂ AND DESORPTION OF ION-RICH SOLUTION

This application is a National Stage application filed under Rule 371 based on PCT/CA2010/001214 filed Aug. 4, 2010 which claims benefit to provisional application 61/231,037 filed Aug. 4, 2009.

FIELD OF INVENTION

The present invention relates generally to $CO_2$ capture and more particularly to a formulation and process for $CO_2$ capture using carbonates and biocatalysts.

BACKGROUND OF THE INVENTION

Increasingly dire warnings of the dangers of climate change by the world's scientific community combined with greater public awareness and concern over the issue has prompted increased momentum towards global regulation aimed at reducing man-made greenhouse gas (GHGs) emissions, most notably carbon dioxide. Ultimately, a significant cut in North American and global $CO_2$ emissions will require reductions from the electricity production sector, the single largest source of $CO_2$ worldwide. According to the International Energy Agency's (IEA) GHG Program, as of 2006 there were nearly 5,000 fossil fuel power plants worldwide generating nearly 11 billion tons of $CO_2$, representing nearly 40% of total global anthropogenic $CO_2$ emissions. Of these emissions from the power generation sector, 61% were from coal fired plants. Although the long-term agenda advocated by governments is replacement of fossil fuel generation by renewables, growing energy demand, combined with the enormous dependence on fossil generation in the near to medium term dictates that this fossil base remain operational. Thus, to implement an effective GHG reduction system will require that the $CO_2$ emissions generated by this sector be mitigated, with carbon capture and storage (CCS) providing one of the best known solutions.

The CCS process removes $CO_2$ from a $CO_2$ containing flue gas, enables production of a highly concentrated $CO_2$ gas stream which is compressed and transported to a sequestration site. This site may be a depleted oil field or a saline aquifer. Sequestration in ocean and mineral carbonation are two alternate ways to sequester that are in the research phase. Captured $CO_2$ can also be used for enhanced oil recovery.

Current technologies for $CO_2$ capture are based primarily on the use of amines solutions which are circulated through two main distinct units: an absorption tower coupled to a desorption (or stripping) tower.

A very significant barrier to adoption of carbon capture technology on large scale is cost of capture. Conventional $CO_2$ capture with available technology, based primarily on the use of amine solvents, is an energy intensive process that involves heating the solvent to high temperature to strip the $CO_2$ (and regenerate the solvent) for underground sequestration. The conventional use of amines involves an associated capture cost of approximately US $60 per ton of $CO_2$ (IPCC), which represents approximately 80% of the total cost of carbon capture and sequestration (CCS), the remaining 20% being attributable to $CO_2$ compression, pipelining, storage and monitoring. This large cost for the capture portion has, to present, made large scale CCS unviable; based on data from the IPCC, for instance, for a 700 megawatt (MW) pulverized coal power plant that produces 4 million metric tons of $CO_2$ per year, the capital cost of conventional $CO_2$ capture equipment on a retrofit basis would be nearly $800 million and the annual operating cost and plant energy penalty would be nearly $240 million. As such, there is a need to reduce the costs of the process and develop new and innovative approaches to the problem.

Due to the high costs associated with amine systems, some work has been done based on carbonate solutions. In such carbonate systems, at pH higher than 10, the predominant mechanism for $CO_2$ absorption is:

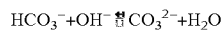

At pH lower than 8, the principal mechanism is:

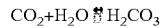

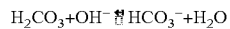

The main advantages of carbonate solutions over amine based solutions are higher capacity, higher stability to oxygen and high temperatures and lower energy requirements for desorption. However, such known carbonate solutions are characterized by a low rate of absorption of $CO_2$ which results in large capture equipment and corresponding capital costs.

Another feature of carbonate based solutions is that, as $CO_2$ reacts with the compound, the product may form precipitates. The presence of solids in the absorption solution enables the shift of the chemical reaction equilibria resulting in a constant $CO_2$ pressure when the loading of the solution increases.

Biocatalysts have also been used for $CO_2$ absorption purposes. More specifically, $CO_2$ transformation may be catalyzed by the enzyme carbonic anhydrase as follows:

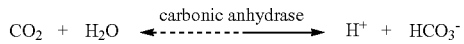

Under optimum conditions, the catalyzed turnover rate of this reaction may reach $1 \times 10^6$ molecules/second.

Carbonic anhydrase has been used as an absorption promoter in amine based solutions to increase the rate of $CO_2$ absorption. Indeed, particular focus has been made on amine solutions for use in conjunction with carbonic anhydrase in $CO_2$ capture processes. One reason why amine solutions have been favoured is that they have relatively low ionic strength, which is a property viewed as significant for carbonic anhydrase hydration activity, since high ionic strength could be detrimental to the stability and function of the protein.

There is a need for a technology that overcomes at least some of the disadvantages of the processes and techniques that are already known, and offers an improvement in the field of $CO_2$ capture.

SUMMARY OF THE INVENTION

The present invention responds to the above mentioned need by providing a formulation, a process and a system for $CO_2$ capture using carbonates and biocatalysts.

More particularly, the present invention provides a process for capturing $CO_2$ from a $CO_2$-containing gas comprising: contacting the $CO_2$-containing gas with an absorption mixture comprising water, biocatalysts and a carbonate compound to enable dissolution and transformation of $CO_2$ into bicarbonate and hydrogen ions, thereby producing a $CO_2$-depleted gas and an ion-rich solution; and subjecting the ion-rich solution to desorption wherein the carbonate compound promotes release of the bicarbonate ions from the ion-rich solution producing a $CO_2$ gas stream and an ion-depleted solution.

In an optional aspect, the process includes removing the biocatalyst from the ion-rich solution prior to subjecting the ion-rich solution to the desorption.

In another optional aspect, the process includes removing the biocatalyst from the ion-rich solution after subjecting the ion-rich solution to the desorption.

In another optional aspect, the process includes recycling the ion-lean solution to form at least a part of the absorption mixture for re-contacting the $CO_2$-containing gas.

In another optional aspect, the process includes adding an amount of biocatalyst into the ion-lean solution to convert the same into at least part of the absorption mixture for recycling to contact the $CO_2$-containing gas.

In another optional aspect, the carbonate compound is selected and used in a sufficient amount in the absorption mixture such that the ion-rich solution contains bicarbonate precipitates.

In another optional aspect, the process includes removing the bicarbonate precipitates from the absorption mixture prior to subjecting the ion-rich solution to the desorption.

In another optional aspect, the bicarbonate precipitates remain in the ion-rich solution upon subjecting the ion-rich solution to the desorption, thereby converting into part of the $CO_2$ gas stream. The bicarbonate precipitates may be composed of bicarbonate species comprising potassium bicarbonate, sodium bicarbonate, ammonium bicarbonate, or a mixture thereof.

In another optional aspect, the carbonate compound comprises potassium carbonate, sodium carbonate or ammonium carbonate, or a combination thereof.

In another optional aspect, the absorption mixture comprises an additional absorption compound. The additional absorption compound may be piperidine, piperazine and derivatives thereof which are substituted by at least one alkanol group, alkanolamines, monoethanolamine (MEA), 2-amino-2-methyl-1-propanol (AMP), 2-(2-aminoethylamino)ethanol (AEE), 2-amino-2-hydroxymethyl-1,3-propanediol (Tris), amino acids, potassium or sodium salts of amino acids, glycine, proline, arginine, histidine, lysine, aspartic acid, glutamic acid, methionine, serine, threonine, glutamine, cysteine, asparagine, valine, leucine, isoleucine, alanine, valine, tyrosine, tryptophan, phenylalanine, and derivatives such as taurine, N,cyclohexyl 1,3-propanediamine, N-secondary butyl glycine, N-methyl N-secondary butyl glycine, diethylglycine, dimethylglycine, sarcosine, methyl taurine, methyl-α-aminopropionic acid, N-(β-ethoxy)taurine, N-(β-aminoethyl)taurine, N-methyl alanine, 6-aminohexanoic acid, or a combination thereof.

In another optional aspect, the process includes contacting the absorption mixture with the $CO_2$-containing gas is performed in an absorption stage comprising at least one reactor selected from a packed tower, a vertical or horizontal spray scrubber, a fluidized bed reactor or a series of reactors comprising the same.

In another optional aspect, a sufficient level of $CO_2$ loading is provided in the absorption stage to promote the precipitation of bicarbonate precipitates.

In another optional aspect, the carbonate compound and biocatalysts are provided in concentrations to achieve a maximum range of relative $CO_2$ transfer rate, with respect to a $CO_2$ transfer rate without biocatalyst. The carbonate compound is preferably provided in the absorption mixture in a concentration of at least about 0.1 M. The carbonate compound may also be provided in the absorption mixture in a concentration at or below saturation thereof.

In another optional aspect, the carbonate compound may comprise potassium carbonate and be provided in the absorption mixture in a concentration up to the solubility limit at a temperature range between about 40° C. and about 70° C.

In another optional aspect, the carbonate compound may comprise ammonium carbonate and be provided in the absorption mixture in a concentration up to the solubility limit at a temperature range between about 10° C. and about 70° C.

In another optional aspect, the carbonate compound may comprise sodium carbonate and be provided in the absorption mixture in a concentration up to the solubility limit at a temperature range between about 40° C. and about 70° C.

In another optional aspect, the biocatalyst is carbonic anhydrase.

In another optional aspect, the biocatalyst is provided free in the water; dissolved in the water; immobilized on the surface of supports that are mixed in the water and are flowable therewith; entrapped or immobilized by or in porous supports that are mixed in the water and are flowable therewith; as cross-linked aggregates or crystals; or a combination thereof. The biocatalysts may preferably be supported by micro-particles that are carried with the water.

The present invention also provides a formulation for capturing $CO_2$ from a $CO_2$-containing gas comprising: a water solvent for allowing dissolution of $CO_2$ therein; biocatalyst for enhancing dissolution and transformation of $CO_2$ into bicarbonate and hydrogen ions into the water solvent; and a carbonate compound in the water solvent in a sufficient amount for promoting the release of the bicarbonate ions dissolved into the water solvent as gaseous $CO_2$ when subjected to desorption.

In one optional aspect, the carbonate compound comprises potassium carbonate, sodium carbonate or ammonium carbonate, or a combination thereof.

In another optional aspect, the carbonate compound is selected and used in a sufficient amount in the absorption mixture to promote precipitation of bicarbonate precipitates.

In another optional aspect, the bicarbonate precipitates are composed of bicarbonate species comprising potassium bicarbonate, sodium bicarbonate, ammonium bicarbonate, or a mixture thereof.

In another optional aspect, the absorption mixture comprises an additional absorption compound. The additional absorption compound may comprise piperidine, piperazine and derivatives thereof which are substituted by at least one alkanol group, alkanolamines, monoethanolamine (MEA), 2-amino-2-methyl-1-propanol (AMP), 2-(2-aminoethylamino)ethanol (AEE), 2-amino-2-hydroxymethyl-1,3-propanediol (Tris), amino acids, potassium or sodium salts of amino acids, glycine, taurine, N,cyclohexyl 1,3-propanediamine, N-secondary butyl glycine, N-methyl N-secondary butyl glycine, alanine, diethylglycine, or dimethylglycine, or a combination thereof.

In another optional aspect, the carbonate compound is provided in the absorption mixture in a concentration of at least about 0.1 M. In another optional aspect, the carbonate compound is provided in the absorption mixture in a concentration at or below saturation thereof.

In another optional aspect, the carbonate compound may comprise potassium carbonate and be provided in the absorption mixture in a concentration up to the solubility limit at a temperature range between about 40° C. and about 70° C.

In another optional aspect, the carbonate compound may comprise ammonium carbonate and be provided in the absorption mixture in a concentration up to the solubility limit at a temperature range between about 10° C. and about 70° C.

In another optional aspect, the carbonate compound may comprise sodium carbonate and be provided in the absorption mixture in a concentration up to the solubility limit at a temperature range between about 40° C. and about 70° C.

In another optional aspect, the biocatalyst is carbonic anhydrase or an analogue thereof.

In another optional aspect, the biocatalyst is provided free in the water; dissolved in the water; immobilized on the surface of supports that are mixed in the water and are flowable therewith; entrapped or immobilized by or in porous supports that are mixed in the water and are flowable therewith; as cross-linked aggregates or crystals; or a combination thereof. The biocatalysts may preferably be supported by micro-particles that are carried with the water.

The present invention also provides a system for capturing $CO_2$ from a $CO_2$-containing gas. The system comprises an absorption unit comprising a gas inlet for the $CO_2$-containing gas, a liquid inlet for providing an absorption mixture comprising a water solvent for allowing dissolution of $CO_2$ therein, biocatalysts for enhancing dissolution and transformation of $CO_2$ into bicarbonate and hydrogen ions into the water solvent, and a carbonate compound in the water solvent in a sufficient amount for promoting the release of the bicarbonate ions dissolved into the water solvent as gaseous $CO_2$ when subjected to desorption. The system comprises a reaction chamber for receiving the absorption mixture and the $CO_2$-containing gas, in which the dissolution and transformation of $CO_2$ into bicarbonate and hydrogen ions occurs. The system comprises a gas outlet for expelling the $CO_2$-depleted gas and a liquid outlet for expelling the ion-rich mixture. The system comprises a regeneration unit for receiving the ion-rich solution and allowing desorption by releasing the bicarbonate ions from the ion-rich solution to produce an ion-depleted solution. The ion-depleted solution may be recycled back into the absorption unit. The system may also have optional features or aspects as described above and hereinbelow.

DESCRIPTION OF PREFERRED EMBODIMENTS OF THE INVENTION

Figure 1:
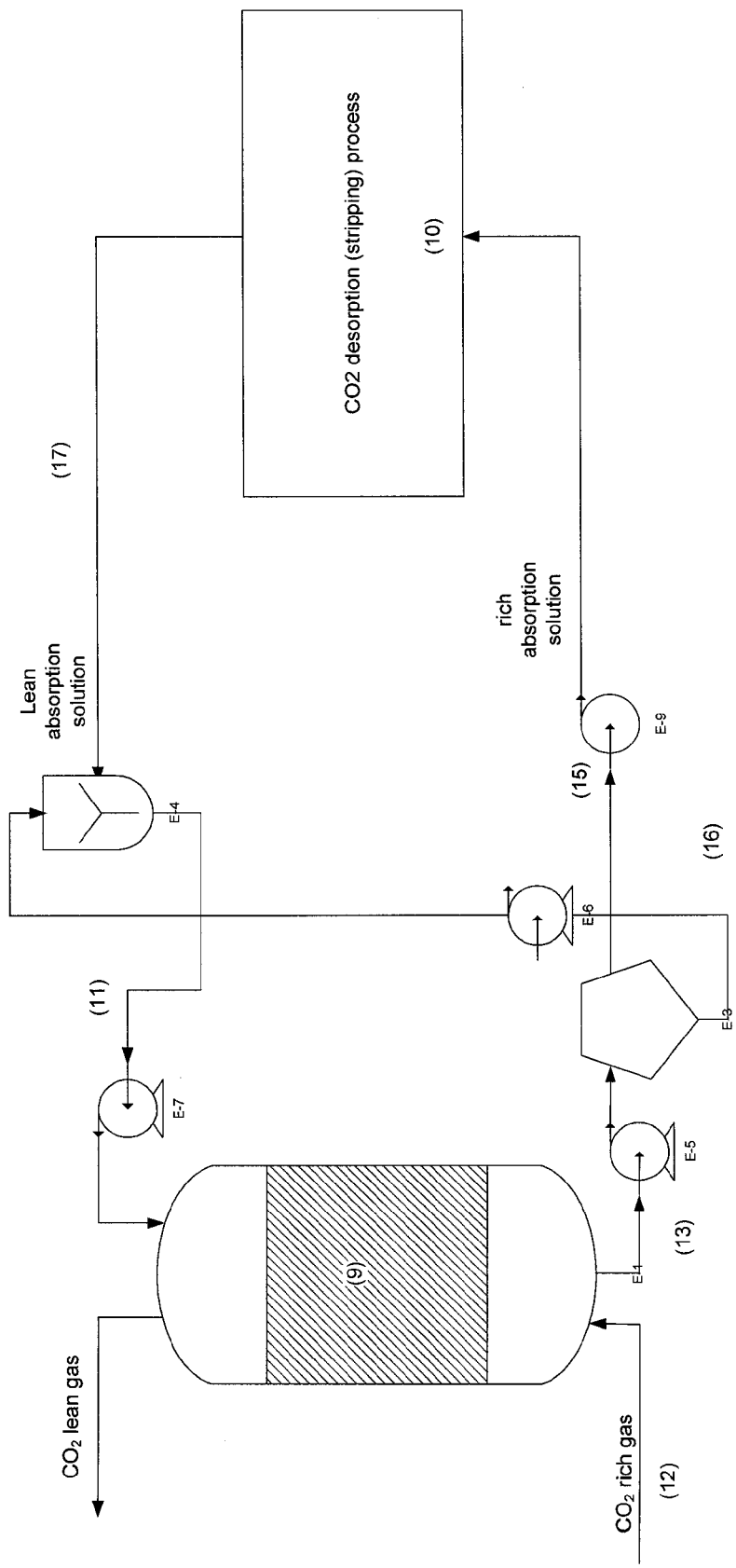
FIG. 1 is a process diagram of an embodiment of the present invention, wherein biocatalytic particles or enzymes flow in the absorption solution.
Figure 2:
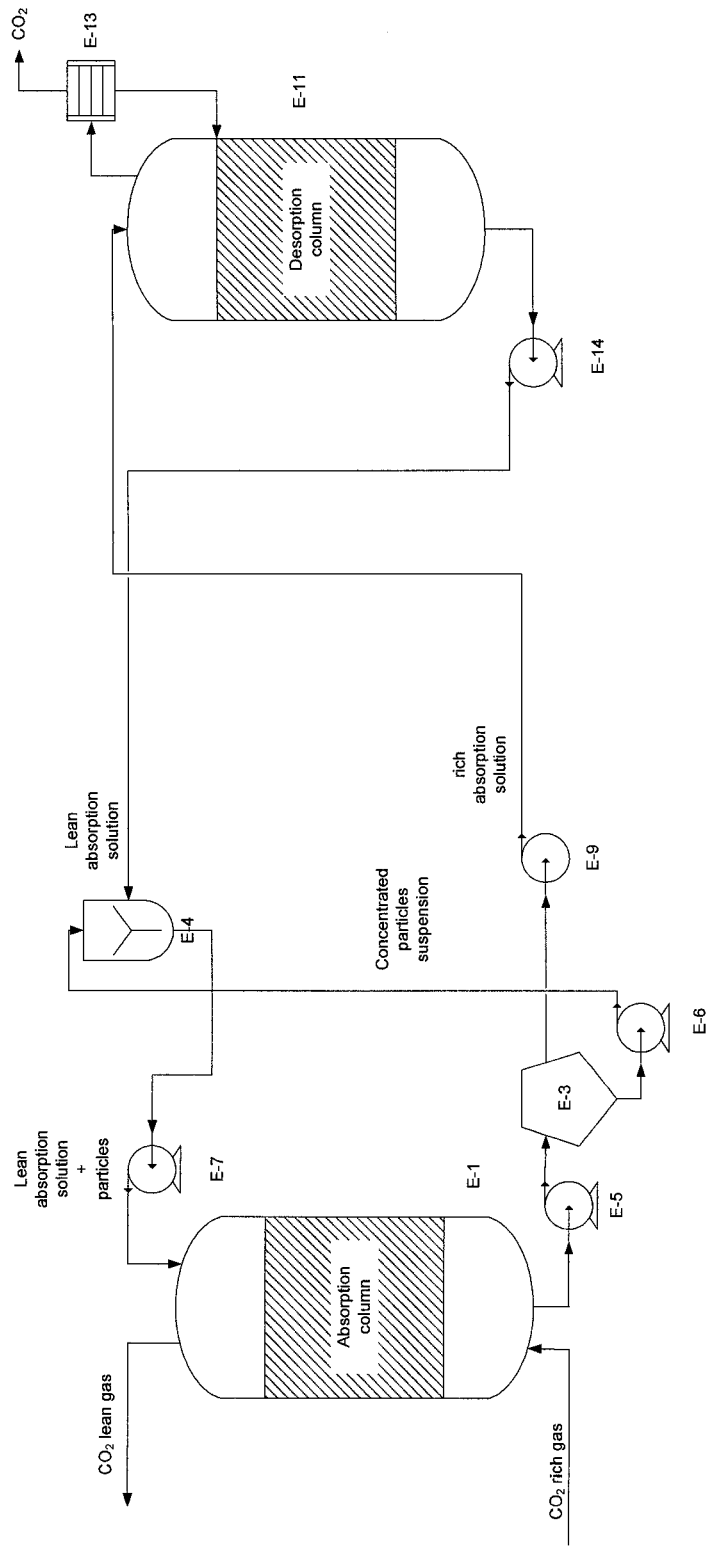
FIG. 2 is a process diagram of another embodiment of the present invention, wherein an absorption unit is coupled to a desorption unit and biocatalytic particles flow in the absorption solution.

FIGS. 1 and 2 respectively show two different embodiments of the process and system of the present invention. It should also be understood that embodiments of the formulation of the present invention may be used in conjunction with the process and system.

In one aspect of the present invention, the formulation comprises water for allowing dissolution of $CO_2$, biocatalyst such as carbonic anhydrase for catalyzing the transformation of $CO_2$ into bicarbonate and hydrogen ions into the water, and carbonate compounds. These components may be provided as a pre-mixed solution or for mixing on site during the $CO_2$ capture operation. Carbonate compounds promote the release of the bicarbonate ions from the water solvent during desorption. Thus, the absorption step of the $CO_2$ capture process is improved due to the activation ability of the biocatalysts and the desorption step is rendered more efficient by virtue of the predominance of carbonate compounds. This improvement aids in enhancing the overall $CO_2$ capture process.

In one embodiment of the invention, the carbonate compound is of the type and is added in sufficient quantities to promote precipitation of a bicarbonate species during absorption. The process parameters may be controlled to further promote such precipitation. The carbonates may be chosen such that the corresponding precipitates have characteristics making them easy to handle with the overall process, by allowing them to be suspended in the reaction solution, pumped, sedimented, etc., as the case may be. The precipitates may be part of the ion-rich solution that is sent for desorption or treated separately for conversion into $CO_2$ gas. More particularly, the precipitates may be bicarbonate species, such as $KHCO_3$, $NaHCO_3$ or $NH_4HCO_3$, and the carbonate compounds may be chosen to allow precipitation of such species.

In another embodiment of the invention, the carbonate compounds also enable lower energy process parameters for desorption. In one embodiment, when the enzymes are provided on or in particles flowing with the solution, the particles may be removed from the ion-rich solution before the ion-rich solution is fed into the desorption unit. Due to their nature and method of immobilisation on the particles, the biocatalysts may be more or less vulnerable to high temperatures. Thus, when desorption is operated at temperatures that could denature the given biocatalysts, the particles are preferably removed before desorption and recycled back into the absorption unit. The carbonates remain in the solution and enhance desorption. It may be preferred that the particles are provided such that they may be easily separated from the bicarbonate precipitate, if need be. In another embodiment, when the biocatalysts are allowed to be present during desorption, the desorption is preferably operated at pressures and temperatures that are tolerable for the given biocatalyst so that the biocatalysts retain their activity, increase desorption rate by catalyzing bicarbonate ion dehydration and can be recycled back into the absorption unit. Desorption may be managed in such cases by reducing the pressure rather than raising the temperature.

In one optional aspect, the biocatalysts in the absorption mixture may be enzymes and more particularly carbonic anhydrase.

In one other embodiment of the invention, the biocatalysts include carbonic anhydrase to enhance performance of absorption solutions for $CO_2$ capture. The enzyme may be provided directly as part of a formulation or may be provided in a reactor to react with incoming solutions and gases. For instance, the enzyme may be fixed to a solid non-porous packing material, on or in a porous packing material, on or in particles flowing with the absorption solution within a packed tower or another type of reactor. The carbonic anhydrase may be in a free or soluble state in the formulation or immobilised on particles within the formulation. It should be noted that enzyme used in a free state may be in a pure form or may be in a mixture including impurities or additives such as other proteins, salts and other molecules coming from the enzyme production process. Immobilized enzyme free flowing in the absorption solution could be entrapped inside or fixed to a porous coating material that is provided around a support that is porous or non-porous. The enzymes may be immobilised directly onto the surface of a support (porous or non porous) or may be present as "cross linked enzymes aggregates" (CLEA) or "cross linked enzymes crystals" (CLEC). CLEA comprise precipitated enzyme molecules forming aggregates that are then crosslinked using chemical agents. The CLEA may or may not have a 'support' or 'core' made of another material which may or may not be magnetic. CLEC comprise enzyme crystals and cross linking agent and may also be associated with a 'support' or 'core' made of another material. When a support is used, it may be made of polymer, ceramic, metal(s), silica, solgel, chitosan, cellulose, magnetic particles and/or other materials known in the art to be suitable for immobilization or enzyme support. When the enzymes are immobilised or provided on particles, such as micro-particles, the particles are preferably sized and provided in a particle concentration such that they are pumpable with the absorption solution. Biocatalysts may also be provided both fixed within the reactor (on a packing material, for example) and flowing with the formulation (as free enzymes, on particles and/or as CLEA or CLEC), and may be the same or different biocatalysts. One of the ways carbonic anhydrase enhances performance of carbonate solutions is by reacting with dissolved $CO_2$ and maintaining a maximum $CO_2$ concentration gradient between gas and liquid phases and then maximizing $CO_2$ transfer rate from the gas phase to the solution. The carbonate compounds may also enable the precipitation of precipitates to further improve the $CO_2$ concentration gradient between gas and liquid phases and thus further increasing $CO_2$ transfer rate.

The biocatalysts may be provided using means depending on the concentration and type of carbonate compound, the process operating parameters, and other factors. For instance, when a high concentration of carbonate compounds is provided, the enzymes may be immobilised on a support to reduce the possibility of deactivation by the carbonates. In some embodiments, the biocatalysts may be advantageously immobilised in a micro-porous structure (which may be a support or a material coating a support) allowing access of $CO_2$ while protecting it against high concentrations of carbonate compounds.

In one optional aspect of the present invention, the carbonate compounds used in the formulation may include potassium carbonate, sodium carbonate, ammonium carbonate, promoted potassium carbonate solutions and promoted sodium carbonate solutions or promoted ammonium carbonate or mixtures thereof.

The following are some advantages, improvements and/or features of some embodiments of the present invention:

The absorption solution is given an increased $CO_2$ absorption rate.

Introducing biocatalysts into carbonate solutions increases the absorption rate of carbonates, coupled with the regeneration efficiencies, to levels which will be advantageous over existing amine based processes.

The enhanced increase of $CO_2$ absorption and relative transfer rates and decrease of energy required for desorption provide an advantageous overall $CO_2$ capture process. This is a major step to bringing such technologies to their industrial application in post combustion $CO_2$ capture. Without the biocatalysts, carbonate absorption solutions would have very limited viability as alternative $CO_2$ capture processes, losing benefits of stability, cost, low volatility, etc.

Biocatalyst-enhanced carbonate-based $CO_2$ capture systems offer significant advantages over conventional processes including lower energy consumption, higher operating stability, lower consumables costs and reduced environmental footprint. As a predominance of bicarbonates rather than carbamates is formed upon $CO_2$ absorption into the carbonate solution, the subsequent production of pure $CO_2$ during the desorption phase requires less energy due to the weak affiliation of $CO_2$ with the solution. As such, lower temperature desorption may be achieved, resulting in the potential for using less expensive, lower grade steam from the power plant operation rather than costly high-grade steam typical of amine-based processes. The potential lower temperature in the desorption stage may also give rise to another advantage in that biocatalysts may also be used in the desorption stage with lower risk of denaturing. In a carbonate system without biocatalysts, slow absorption kinetics which would demand large absorption vessels and correspondingly high capital costs, negating the low energy of desorption. Hence, the biocatalyst provides an important enabling feature by accelerating the absorption rate to allow for the use of the low-energy carbonate solution while reducing the size of the absorption equipment. In addition, conventional amine-based $CO_2$ capture systems can suffer from a lack of stability of the amine solution which can be susceptible to oxygen and contaminants in the power plant flue gas, such as sulphur dioxide ($SO_2$). This results in the situation where either inhibitors need to be added or additional pre-treatment of the flue gas is required, increasing the cost and complexity of the system. As a result of higher stability of carbonates, solution makeup may be required on a less frequent basis, further improving the economics of the process in this case. Additionally, carbonate solutions, namely potassium and sodium carbonate, are less costly to procure than amine solvents. Carbonate solutions possess relatively favourable environmental properties. Potassium and sodium carbonate solutions are relatively benign when compared to amine solutions, significantly reducing the potential for toxic events and limiting any water and waste treatment related issues. Overall, the above advantages of carbonate solvents can provide for an attractive operating scenario, providing that absorption can be enhanced to meet the requirements for an economic rate of capture, which the biocatalysts enable.

In addition, the combination of the concentration of carbonate solution with the concentration of biocatalysts relative to a specific $CO_2$ loading is a further feature of some optional aspects of the process, which can enable reaching an optimum range of relative $CO_2$ transfer rate during absorption. The optimum range can be defined in a number of ways and should not be limited to a specific point. The optimum range may be defined as a range containing the maximum value for $CO_2$ relative transfer rate with a certain standard deviation, as a range of values around the actual maximum at which the process is economically viable, or defined in other ways. Illustrations of maximum or optimum ranges are illustrated in various examples hereinbelow.

One embodiment of the process and system is shown in FIG. 1 and will be described in further detail hereafter. First, the biocatalysts, which may be provided on or in particles, are added to the lean absorption solution in a mixing chamber (E-4). The lean absorption solution refers to the absorption solution characterized by a low concentration of the species to be absorbed. This solution is either fresh solution or comes from the mineral carbonation process or the $CO_2$ desorption process (10). The absorption solution with biocatalysts (11) is then fed to the top of a packed column (E-1) with a pump (E-7). The packing material (9) may be made of conventional material like polymers, metal and ceramic. The geometry of the packing may be chosen from what is commercially available. It is also possible to chose or arrange the packing to promote certain deflections and collisions with the micro-particles, or to avoid accumulation of the micro-particles within the reactor. For instance, the packing preferably has limited upward facing concavities to avoid the accumulation of micro-particles therein. Also preferably, the micro-particles and packing are chosen so that the micro-particles can flow through the reactor without clogging. In some alternative embodiments, the biocatalysts can be provided on the packing rather than in the absorption mixture. Counter-currently, a $CO_2$ containing gas phase (12) is fed to the packed column (E-1) and flows on, through, and/or around the packing (9) from the bottom to the top of the column. The absorption mixture with biocatalysts that may be supported by particles and carbonate solution flows on, through, and/or around the packing material (9) from the top of the column to the bottom. As the absorption mixture and biocatalytic micro-particles progress on, through, and/or around the packing, the absorption solution becomes richer in the compound that is being absorbed, which is $CO_2$. Biocatalysts, present near the gas-liquid interface, enhance $CO_2$ absorption by immediately reacting with $CO_2$ to produce bicarbonate ions and protons and thus maximizing the $CO_2$ concentration gradient across the interface. At the exit of the column, the rich absorption mixture containing the biocatalysts and bicarbonates ions (13) are pumped (E-5) to a particle separation unit (E-3). Rich absorption solution refers to the absorption mixture characterized by a concentration of absorbed compound which is higher than that of the lean solution. The separation unit may comprise a filtration unit (such as a tangential filtration unit), a centrifuge, a cyclone, a sedimentation tank or a magnetic separator and any other units or equipments known for particle or solid separation. The separation unit also enables a certain quantity of solution to be retained with the biocatalytic micro-particles so they do not dry out which can denature the biocatalysts. In one optional aspect, the quantity of retained solution enables the biocatalytic micro-particles to be pumped to a storage unit or directly back to a mixing chamber (E-4) for addition into the absorption unit. In another optional aspect, the biocatalysts with retained solution may be gravity fed into the mixing chamber (E-4), which may be enabled by performing separation above the mixing unit, for example. The separation may be conducted in continuous or in batch mode, and may be managed to ensure the proper amount of solution is retained to ensure enzyme activity. It may also be preferred that the biocatalytic micro-particles are provided such that they may be easily separated from any solid precipitates (e.g. bicarbonate precipitates) that may be entrained in the ion-rich solution, if need be. The absorption mixture without biocatalytic micro-particles (15) is then pumped (E-9) to another process stage such as a regeneration stage, which may include $CO_2$ desorption or mineral carbonation (10). Biocatalytic micro-particles (16) are mixed with the $CO_2$ lean absorption solution. This suspension is then fed once again to the absorption column (E-1).

In another embodiment, the absorption unit is coupled to a desorption unit as shown in further detail in FIG. 2. In this embodiment, the absorption solution rich in $CO_2$ without biocatalytic micro-particles (15) is pumped (E-9) through a heat exchanger (E-10) where it is heated and then sent on to the desorption column (E-11). In the desorption unit, the solution is further heated in order that the $CO_2$ is released from the solution in a gaseous state. Because of relatively high temperature used during desorption, water also vaporizes. Part of the absorption solution (18) is directed toward a reboiler (E-12) where it is heated to a temperature enabling $CO_2$ desorption. Gaseous $CO_2$ together with water vapour are cooled down, water condenses and is fed back to the desorption unit (19). Dry gaseous $CO_2$ (20) is then directed toward a compression and transportation process for further processing. The liquid phase, containing less $CO_2$, and referred to as the lean absorption solution (17) is then pumped (E-14) to the heat exchanger (E-10) to be cooled down and fed to the mixing chamber (E-4). The temperature of the lean absorption solution (17) should be low enough not to denature the enzyme if present.

In another optional aspect of the present invention, if a robust enzyme (biocatalysts robust to desorption conditions) is available, the biocatalysts might also help in improving the rate of $CO_2$ dehydration and thus increasing $CO_2$ desorption rate resulting in smaller desorption equipment. In such a process configuration the biocatalysts may have an impact in the absorption unit by increasing the $CO_2$ absorption rate but also in the desorption unit since an enzyme such as carbonic anhydrase can increase the rate of bicarbonate ion transformation into $CO_2$ (which is one of the reactions that would take place in the desorption unit). In this configuration, the removal unit (E-3) would be required to remove deactivated biocatalysts and unit E-4 to add fresh biocatalysts. However, it may be advantageous to have a separation unit such as a filter between (E-11) and (E-12) to avoid flow of biocatalysts through the reboiler and their contact with very high temperatures (depending on the thermoresistance of the enzymes).

The mixing chamber (E-4) preferably comprises an inlet for receiving recycled biocatalysts from the separation unit (E-3) and also an inlet/outlet for both removing a fraction of deactivated biocatalysts and replacing them with new fresh biocatalyst, thereby refurbishing the overall batch of biocatalysts in the system. In some embodiments, biocatalysts are filtered, centrifuged, cycloned, sedimented or separated magnetically in a first separation unit (according to their above-mentioned support system) and other small particles such as bicarbonate precipitates can be separated in a preceding or subsequent separation unit.

In one embodiment, biocatalysts are used in conjunction with additional absorption compounds in the absorption mixture. The absorption compounds may be primary, secondary and/or tertiary amines (including alkanolamines); and/or primary, secondary and/or tertiary amino acids. The absorption compound may more particularly include amines (e.g. piperidine, piperazine and derivatives thereof which are substituted by at least one alkanol group), alkanolamines (e.g. monoethanolamine (MEA), 2-amino-2-methyl-1-propanol (AMP), 2-(2-aminoethylamino)ethanol (AEE), 2-amino-2-hydroxymethyl-1,3-propanediol (Tris), N-methyldiethanolamine (MDEA), dimethylmonoethanolamine (DMMEA), diethylmonoethanolamine (DEMEA), triisopropanolamine (TIPA) and triethanolamine), dialkylether of polyalkylene glycols (e.g. dialkylether or dimethylether of polyethylene glycol); amino acids which may include potassium or sodium salts of amino acids, glycine, taurine, N-cyclohexyl 1,3-propanediamine, N-secondary butyl glycine, N-methyl N-secondary butyl glycine, alanine, diethylglycine, dimethylglycine, methionine, alanine, proline, and/or sarcosine; and/or mixtures thereof. Absorption compounds are added to the solution to aid in the $CO_2$ absorption and to combine with the catalytic effects of the carbonic anhydrase. Due to the structure or high concentration of some absorption compounds, the activity or longevity of the carbonic anhydrase can be threatened. For instance, free enzymes may be more vulnerable to denaturing caused by an absorption compound with high ionic strength. Immobilising the carbonic anhydrase can mitigate the negative effects of such absorption compounds. By providing enzymes immobilised on a support material, such as for example on micro-particles, the process can yield high $CO_2$ transfer rates in the presence of absorption compounds while mitigating the negative effects such compounds could otherwise have on free enzymes.

EXAMPLES

The following examples present different ways to activate absorption solutions with carbonic anhydrase and generally elaborate on the embodiments of the present invention.

Example 1

An experiment was conducted in an absorption packed column. The absorption solution is an aqueous solution of potassium carbonate ($K_2CO_3$) 20% (w/w) (equivalent to 1.45 M). This absorption solution is contacted counter-currently with a gas phase with a $CO_2$ concentration of 130,000 ppm. Liquid flow rate was 0.6 g/min and gas flow rate was 60 g/min corresponding to L/G of 10 (g/g). Gas and absorption solution were at room temperature. Operating pressure of the absorber was set at 1.4 psig. The column has a 7.5 cm diameter and a 50 cm height. Packing material is polymeric Raschig rings 0.25 inch. Three tests were performed: the first with no biocatalyst, the second with carbonic anhydrase biocatalyst immobilized to packing support and the third using carbonic anhydrase free in solution at a concentration of 0.5 g per liter of solution.

The results obtained showed that $CO_2$ transfer rate or $CO_2$ removal rate increased from 3 to 14 mmol $CO_2$/min with carbonic anhydrase immobilized onto the surface of Raschig rings. Using free enzymes i.e carbonic anhydrase free flowing in the absorption solution, $CO_2$ transfer rate increased up to 37 mmol/min. These results indicate that under tested conditions, $CO_2$ transfer rate can be increased by more than 5 fold using free or immobilized enzymes in the same equipment.

Example 2

An experiment was conducted in an absorption packed column. The absorption solution is an aqueous solution of sodium carbonate ($Na_2CO_3$) 0.5M. This absorption solution is contacted counter-currently with a gas phase with a $CO_2$ concentration of 130,000 ppm. Liquid flow rate was 0.65 g/min and gas flow rate was 65 g/min corresponding to L/G of 10 (g/g). Gas and absorption solution were at room temperature. Operating pressure of the absorber was set at 1.4 psig.

The column has a 7.5 cm diameter and a 50 cm height. Packing material is polymeric Raschig rings 0.25 inch. Three tests were performed: the first with no biocatalyst, the second with carbonic anhydrase immobilized to packing support and the third using carbonic anhydrase free in solution at a concentration of 0.5 g per liter of solution.

The results obtained showed that $CO_2$ transfer rate or $CO_2$ removal rate increased from 5 to 18 mmol $CO_2$/min with carbonic anhydrase immobilized onto the surface of Raschig rings. In the presence of free enzyme i.e. carbonic anhydrase free flowing in the solution, the transfer rate increased to 38 mmol/min. These results clearly demonstrate the positive impact of adding the enzyme in a packed column.

Example 3

An experiment was conducted in an absorption packed column. The absorption solution is an aqueous solution of ammonium carbonate $(NH_4)_2CO_3/(NH_4)OH$ 8M (ammonium). This absorption solution is contacted counter-currently with a gas phase with a $CO_2$ concentration of 130 000 ppm. Liquid flow rate was 0.25 g/min and gas flow rate was 63 g/min corresponding to L/G of 4 (g/g). Gas and absorption solution were at room temperature. Operating pressure of the absorber was set at 1.4 psig. The column has a 7.5 cm diameter and a 50 cm height. Packing material is polymeric Raschig rings 0.25 inch. Two tests were performed: the first with no biocatalyst, and the second using carbonic anhydrase immobilized to packing.

The results obtained showed that $CO_2$ transfer rate or $CO_2$ removal rate increased from 190 to 216 mmol $CO_2$/min with carbonic anhydrase immobilized onto the surface of Raschig rings. In this case, the absorption performance is increased by 14% under tested operating conditions.

Example 4

Figure 3:
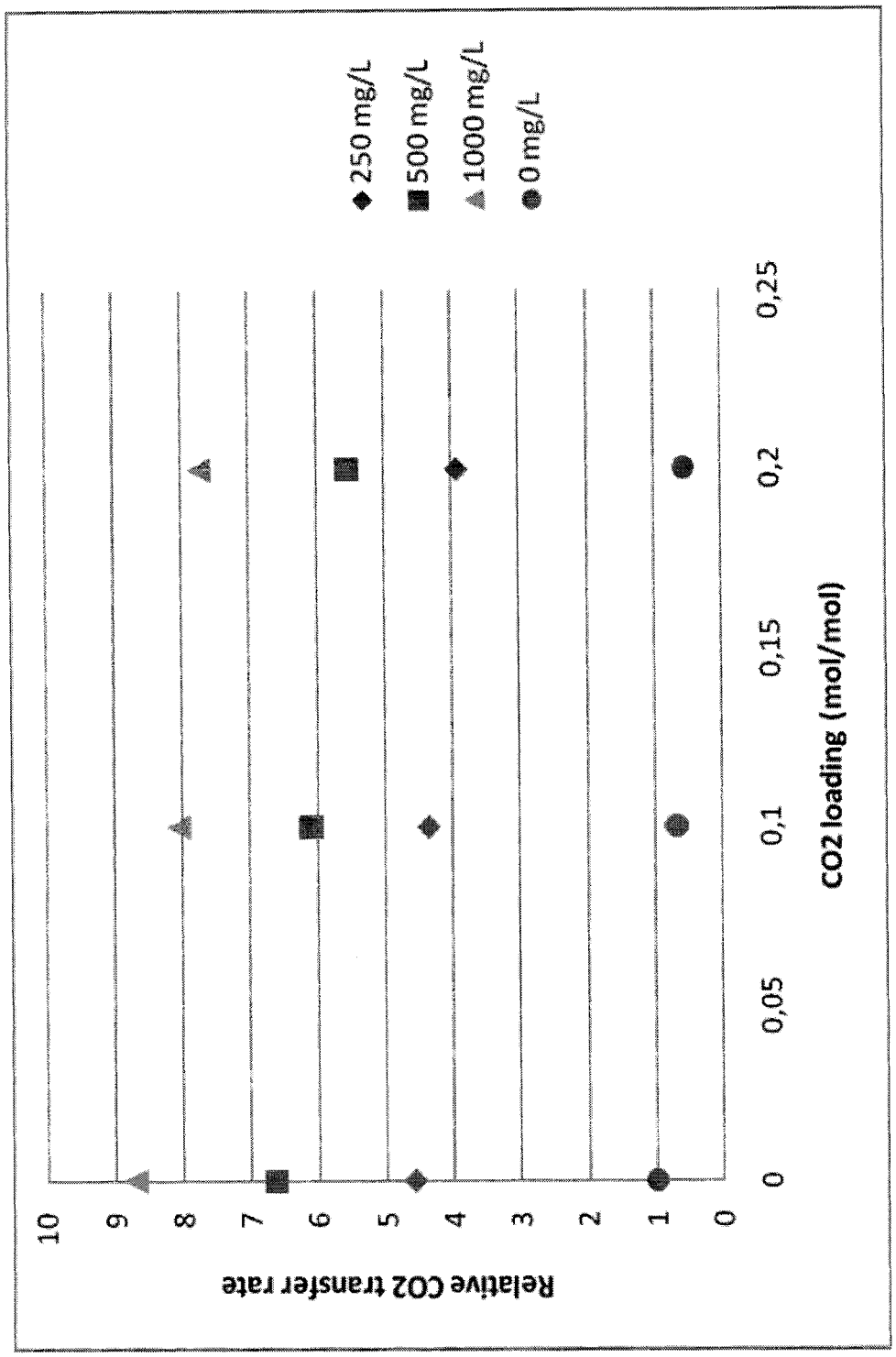
FIG. 3 is a graph of relative $CO_2$ transfer rate for carbonic anhydrase concentration ranging from 0 to 1000 mg/L in a 1.45 M $K_2CO_3$ solution with $CO_2$ loading ranging from 0 to 0.2 mol/mol.

To demonstrate the impact of free carbonic anhydrase, tests were conducted in a stirred cell at enzyme concentrations of 250, 500 and 1000 mg/L in a 1.45 M $K_2CO_3$ solution at a temperature of 25° C. Initial $CO_2$ loading of the solution was adjusted to 0, 0.1 and 0.2 mol $CO_2/K_2CO_3$. Enzyme used is a variant of human carbonic anhydrase type-II, designated as 5X (this enzyme contains five genetic mutations as compared to the original enzyme). $CO_2$ absorption tests are performed in a stirred cell, a simple device that can be used to evaluate $CO_2$ absorption rates under different conditions. The stirred cell contains the absorption solution (and the enzyme when required). A known pressure of pure $CO_2$ is applied to the solution, the pressure corresponds to the $CO_2$ partial pressure that can be found in an industrial post-combustion flue gas. In these tests, initial $CO_2$ pressure is 200 mbar. Then the pressure decrease is monitored and used to calculate $CO_2$ transfer rate in the absorption. Tests were conducted with and without enzyme to enable determination of the enzyme impact. Results are expressed as a ratio of the $CO_2$ transfer rate with enzyme to the $CO_2$ transfer rate in the absence of the enzyme (see FIG. 3). Results clearly indicate that adding enzyme to the 1.45 M $K_2CO_3$ solution brings an important benefit for all tested conditions. Impact is more important when the enzyme concentration is higher. Results also indicate that the $CO_2$ loading of the solution has an impact on the improvement brought by the enzyme. The impact obtained in stirred cells is similar to that obtained in a packed column (see Example 2). It is assumed, as for other system reported in literature, that we could predict from stirred cell results the impact of the enzyme in a packed column.

Example 5

Figure 4:
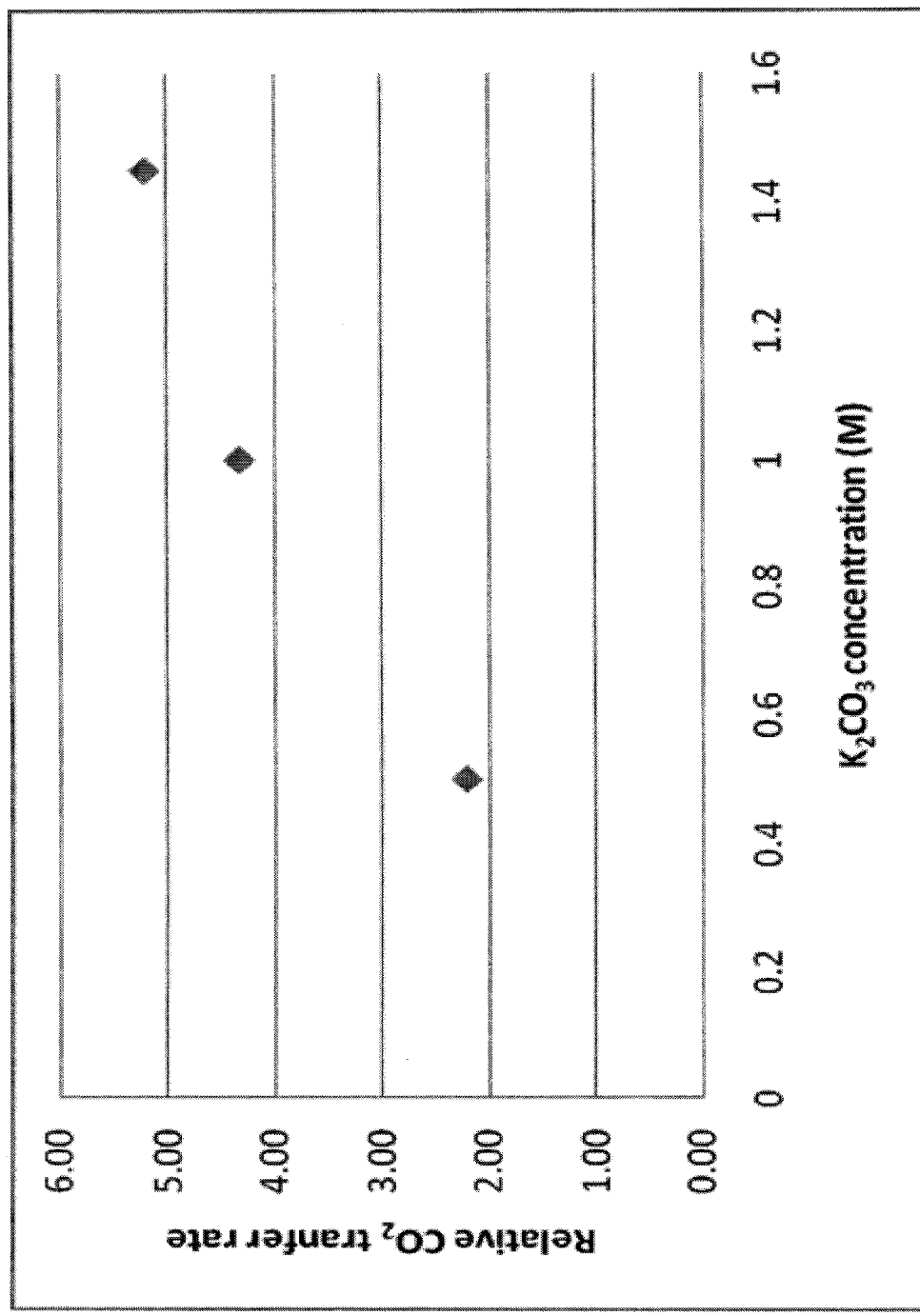
FIG. 4 is a graph of relative $CO_2$ transfer rate for 500 mg/L Human Carbonic Anhydrase Type-II (HCAII) in $K_2CO_3$ solutions at concentrations of 0.5, 1 and 1.45 M.

Tests were conducted in a hydration cell at an enzyme concentration of 500 mg/L in $K_2CO_3$ solutions with concentrations of 0.5, 1 and 1.45 M at a temperature of 20° C. Enzyme used is human carbonic anhydrase type II. Initial $CO_2$ loading is 0 mol $CO_2$/mol $K_2CO_3$. The hydration cell and testing methods are different from the one described in Example 4 in that a continuous flow of pure $CO_2$ is flushed in this cell at a pressure of 1 atma, at the surface of the liquid phase (with or without enzyme) and pH change of the solution is monitored. Changes in pH are correlated to changes in inorganic carbon concentration which are used to calculate $CO_2$ transfer rates. Results are expressed as a ratio of $CO_2$ transfer rate with enzyme to $CO_2$ transfer rate in the absence of the enzyme (see FIG. 4). It is important to note, that as such, as the hydration cell is used for more rapid, indicative testing of enzyme catalytic activity, the corresponding results are not viewed to be as precise as those obtained in Example 4. This fact generally explains any variation in observed results between the two testing systems under similar conditions. Results clearly indicate that enzyme brings an important benefit for all tested $K_2CO_3$ solutions.

Example 6

Tests were conducted in a hydration cell at an enzyme concentration of 500 mg/L in $K_2CO_3$ solutions at concentrations of 0.5 and 1.45 M at a temperature of 40° C. (method is as described in Example 5). Enzyme used is the variant 5X. Initial $CO_2$ loading is 0 mol $CO_2$/mol $K_2CO_3$. Results indicate that under these experimental conditions enzyme brings a benefit for the 1.45 $K_2CO_3$ solution only (Table 1), indicating that temperature may have an influence on the impact of the enzyme on $CO_2$ absorption rate.

TABLE 1

Relative $CO_2$ transfer rates in $K_2CO_3$ solutions at a temperature of 40° C. with an enzyme concentration of 500 mg/L.

| $K_2CO_3$ concentration (M) | Relative Transfer rate |
|---|---|
| 0.5 | 1 |
| 1.45 | 2.1 |

Example 7

Figure 5:
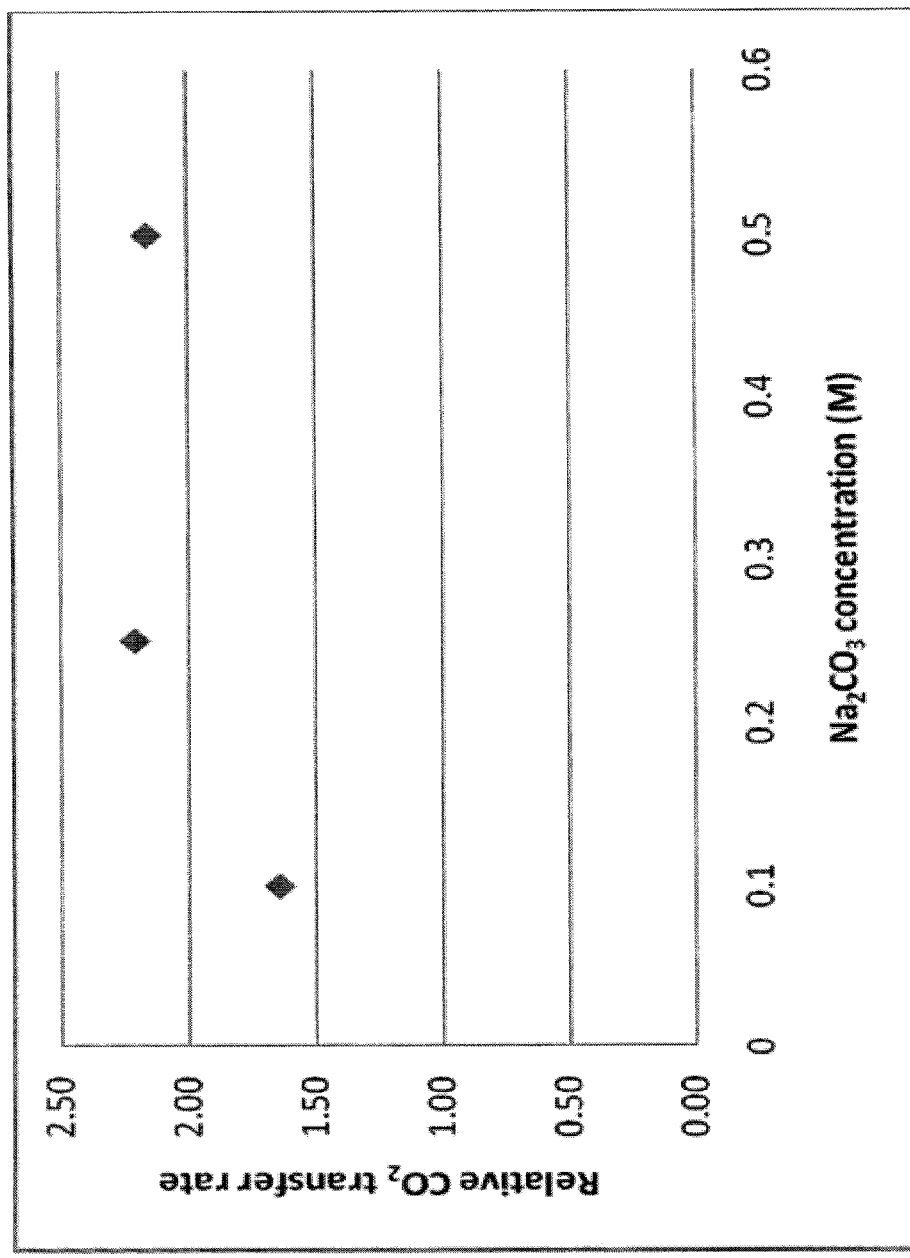
FIG. 5 is a graph of relative $CO_2$ transfer rate for 500 mg/L HCAII in $Na_2CO_3$ solutions at concentrations of 0.1, 0.25 and 0.5 M.

Tests were conducted in a hydration cell at an enzyme concentration of 500 mg/L in $Na_2CO_3$ solutions with concentrations of 0.1, 0.25 and 0.5 M at a temperature of 20° C. Method is described in Example 5. Enzyme used is HCAII. Initial $CO_2$ loading is 0 mol $CO_2$/mol $Na_2CO_3$. Results are expressed as a ratio of $CO_2$ transfer rate with enzyme to $CO_2$ transfer rate in the absence of the enzyme (see FIG. 5). Results clearly indicate that enzyme brings an important benefit for all tested $Na_2CO_3$ solutions.

Example 8

The impact of free carbonic anhydrase was tested in ammonium carbonate solutions, at different $CO_2$ loadings at temperatures of 10 and 20° C. Ammonium carbonate solutions are prepared from 5 M $NH_3$ solution contacted with pure $CO_2$ to reach particular $CO_2$ loading values. Tests were conducted in a stirred cell at an enzyme concentration of 500 mg/L. Enzyme used is variant 5X. Method and equipment is as described in Example 4. Results are expressed as a ratio of $CO_2$ transfer rate with enzyme to $CO_2$ transfer rate in the absence of the enzyme (see Table 1). Results indicate that the impact of the enzyme may vary depending on the $CO_2$ loading of the solution. Enzyme impact is larger when $CO_2$ loading of the ammonium carbonate solution is higher. At a temperature of 10° C., at a $CO_2$ loading of 0.12, enzyme does not have any impact principally because the free ammonia concentration is high, and thus the solution is so rapid in absorbing $CO_2$ that enzyme contribution is not important. At the loading of 0.36, enzyme increases the $CO_2$ transfer rate by a factor of 1.5. In this case, free ammonia concentration is lower and thus contributes less to $CO_2$ absorption.

TABLE 2

Impact of 500 mg/L of enzyme 5X on the $CO_2$ transfer rate in 5M ammonium carbonate solutions at different $CO_2$ loading values at temperatures of 10 and 20° C.

| Temperature | $CO_2$ Loading (mol $CO_2$/mol $NH_3$) | Relative $CO_2$ transfer rate |
|---|---|---|
| 10° C. | 0.12 | 1.0 |
|  | 0.36 | 1.5 |
| 20° C. | 0.16 | 1 |
|  | 0.48 | 2.3 |

Example 9

The impact of free carbonic anhydrase was tested in a 1.8 M ammonium carbonate solution at a temperature of 10° C. Tests were conducted in a stirred cell at an enzyme concentration of 500 mg/L. Enzyme used is variant 5X. Initial $CO_2$ loading of the solution is 0 mol $CO_2$/mol $NH_3$. Method is as described in Example 4. Results show that enzyme increases the $CO_2$ absorption rate by a factor of 4.5 under these conditions.

Example 10

Figure 6:
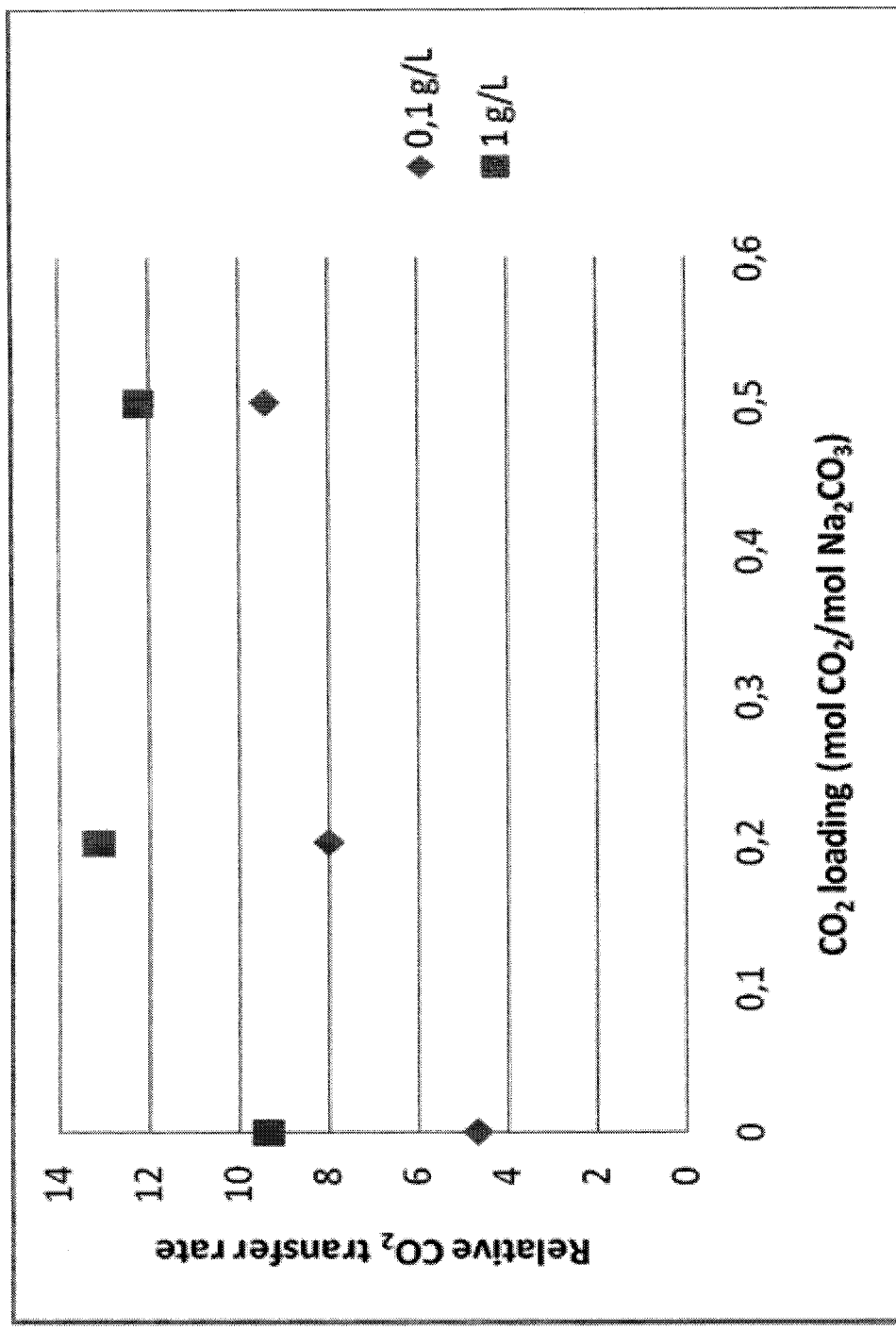
FIG. 6 is a graph of relative $CO_2$ transfer rate in a 0.5 M $Na_2CO_3$ solution at loadings of 0, 0.2 and 0.5 mol $CO_2$/mol $Na_2CO_3$ with enzyme concentrations of 0.1 and 1 g/L.

The impact of free carbonic anhydrase was tested in a 0.5 M $Na_2CO_3$ solution at a temperature of 25° C. Tests were conducted in a stirred cell at enzyme concentrations of 0, 100 and 1000 mg/L and at $CO_2$ loadings of 0, 0.1 and 0.2 mol $CO_2$/mol $Na_2CO_3$. Enzyme used is a variant of human carbonic anhydrase II, designated as 5X. Method is as described in Example 4. Results indicate that increasing enzyme concentration leads to a higher absorption rate for all $CO_2$ loadings (FIG. 6). Results also indicate that enzyme impact reaches a maximum value at an enzyme concentration of approximately 1 g/L.

Example 11

To determine the impact of enzymatic particles on $CO_2$ absorption rate, tests were conducted in the hydration cell. Tests are conducted as follows: a known volume of the unloaded absorption solution is introduced in the reactor, then a know mass of particles are added to the absorption solution (particles may or may not contain enzyme), a $CO_2$ stream is flown through the head space of the reactor and agitation is started. The pH of the solution is measured as a function of time and pH values are then converted into carbon concentration in g carbon/L using a carbon concentration-pH correlation previously determined for the absorption solution. Absorption rates are determined from a plot of carbon concentration as a function of time. Impact of the enzyme is reported as a relative absorption rate: The ratio of absorption rate in the presence of the enzyme particles to the absorption rate in the presence of particles without enzyme.

Example 12

Tests were conducted with HCAII immobilised at the surface of nylon particle (non optimised protocol). Nylon particles size ranges from 50-160 microns. Absorption solutions were 1.45 M $K_2CO_3$ and 0.5 M $Na_2CO_3$. Testing temperature was 20° C. Method was as described in Example 11. Results indicate that $CO_2$ absorption rate was increased by 20-30% for both solutions.

Example 13

Tests were conducted with cross linked enzyme aggregates (CLEA) of carbonic anhydrase (non optimized protocol). The enzyme used is a thermoresistant variant of enzyme HCAII, designated as 5X. CLEA contains 26% (w/w) of the 5X enzyme. Particle size ranges between 4-9 microns. The absorption solution was 1.45 M $K_2CO_3$. Testing temperature was 20° C. Enzyme concentration in the solution was 0.5 g/L. Method is described in Example 11. In this particular case, denatured enzyme particles were used as the reference. Results indicate that CLEAs increases $CO_2$ absorption rate by a factor of 3.2 in the $K_2CO_3$.

Example 14

Tests were conducted with HCAII immobilised at the surface of magnetic silica coated iron oxide particles (non optimised protocol). Particle size is 5 microns. Absorption solution was 1.45 M $K_2CO_3$. Testing temperature was 20° C. Enzyme concentration is 0.2 g/L. Method is described in Example 5. Results indicate that enzyme on magnetic particles increases $CO_2$ absorption rate by a factor of 1.6.

Example 15

The impact of free carbonic anhydrase was tested in a 0.3 M $Na_2CO_3$/1.2 M $K_2CO_3$ solution at a temperature of 20° C. Tests were conducted in a hydration cell at an enzyme concentration of 500 mg/L and at $CO_2$ loading of 0 mol/mol. Enzyme used is a variant of human carbonic anhydrase II, designated as 5X. Method is as described in Example 5. Results indicate that the enzyme leads to an increase in the $CO_2$ absorption rate of 3.7 fold. Thus carbonic anhydrase also increases $CO_2$ absorption rates in carbonate mixtures.

Example 16

The impact of carbonic anhydrase was compared for different potassium carbonate solutions having concentrations of 0, 0.5, 1.0 and 1.45 M. To take into account for the fact that carbonate solutions are alkaline, the zero concentration was prepared with water by adjusting pH to 12 using NaOH. Then for each solution, $CO_2$ transfer rate was measured in a hydration cell (Example 5) in absence of carbonic anhydrase and in presence of an enzyme concentration of 0.5 g/L. Tests were conducted at 20° C. Results are shown in Table 3 and in FIG. 7. We can observe that for a similar pH, presence of $K_2CO_3$ considerable increase $CO_2$ transfer rate. It can also be observed that as potassium carbonate concentration is higher than 0.5 M $CO_2$ transfer rates decrease. Addition of the enzyme to these solutions resulted in all cases in an increase in $CO_2$ transfer rates. However highest impact was obtained at 1.0M. In selecting the best operation conditions will be a compromise between the impact of the enzyme and the solution capacity another important parameter in post combustion $CO_2$ capture processes.

TABLE 3

$CO_2$ transfer rates in potassium carbonate solutions in presence of 0.5 g/L of carbonic anhydrase

| Concentration (M) | $CO_2$ transfer rate w/o enzyme (Blank) (g carbon/L · s) | $CO_2$ transfer rate with enzyme (g carbon/L · s) |
|---|---|---|
| 0 | $2 \times 10^{-6}$ | $2.4 \times 10^{-6}$ |
| 0.5 | $5.9 \times 10^{-5}$ | $1.3 \times 10^{-4}$ |
| 1.0 | $3 \times 10^{-5}$ | $1.3 \times 10^{-4}$ |
| 1.45 | $1.4 \times 10^{-5}$ | $7.3 \times 10^{-5}$ |

Example 17

To take advantage of biocatalysts flowing in the absorption solution (free or immobilized on/in particles flowing in the absorption solution or as CLEAs or CLECs) for gas scrubbing especially for $CO_2$ removal from a $CO_2$ containing effluent, one process embodiment configuration is shown in FIG. 1. First, the biocatalytic particles are mixed in the lean absorption solution in a mixing chamber (E-4). The biocatalytic particles have a size enabling their flow on, through, and/or around the packing of the packed column without clogging. The lean absorption solution refers to the absorption solution characterized by a low concentration of the species to be absorbed. This solution is either fresh solution or comes from the $CO_2$ desorption process (1). The absorption solution with biocatalytic particles (11) is then fed to the top of a packed column (E-1) with a pump (E-7). The packing material (9) may be made of conventional material like polymers, metal and ceramic. The geometry of the packing may be chosen from what is commercially available. The packing preferably is chosen to have geometry or packing arrangement, to facilitate the flow of small particles present or generated in the absorption solution. Examples of packing are: Pall rings, Raschig rings, Flexipak, Intalox, etc. Counter-currently, a $CO_2$ containing gas (12) is fed to the packed column (E-1) and flows through the packing (9) from the bottom to the top of the column. The absorption solution and biocatalytic particles flow through the packing material (9) from the top of the column to the bottom. As the absorption solution and biocatalytic particles flow on, through, and/or around the packing, the absorption solution becomes richer in the compound that is being absorbed, in this case $CO_2$. Biocatalytic particles, present near the gas-liquid interface, enhance $CO_2$ absorption by immediately reacting with $CO_2$ to produce bicarbonate ions and protons and thus maximizing the $CO_2$ concentration gradient across the gas-liquid interface. At the exit of the column, the rich absorption solution and biocatalytic particles (13) are pumped (E-5) to a particle separation unit (E-3). Rich absorption solution refers to the absorption solution characterized by a concentration of absorbed compound which is higher than that of the lean solution. The separation unit may consist of a filtration unit, a centrifuge, a sedimentation tank, magnetic separator and/or any other units or equipment known for particles or solid separation. The absorption solution without particles (15) is then pumped (E-9) to another unit which may be a $CO_2$ desorption unit (10). Biocatalytic particles (16) are pumped (E-6) to a mixing chamber (E-4) where they are mixed with the $CO_2$ lean absorption solution. The mixing chamber may be equipped with an impeller or another device which function is to assure that biocatalytic particles are mixed and/or suspended in the absorption solution which is then pumped (E-7) once again to the absorption column (E-1).

Example 18

In the case that enzymes are immobilized on the surface of packing material only, the process may be slightly different from the one shown in FIG. 1. For such a case, units E-3, E-4, E-6 and E-9 may not be present since they are required for the processing of the biocatalytic particles in the absorption solution.

Example 19

In one embodiment, the absorption unit is coupled to a desorption unit as shown in further detail in FIG. 2. In this embodiment, the absorption solution rich in $CO_2$ with or without biocatalytic particles (15) is pumped (E-9) to the desorption column (E-11) operated at a lower pressure than the absorption. In the desorption unit, the decrease in pressure and/or increase in temperature causes that the $CO_2$ is released from the solution in a gaseous state. Because of relatively low pressure used during desorption, water also vaporizes. Gaseous $CO_2$ together with water vapour are cooled down, water condenses and is fed back to the desorption unit (19). Dry gaseous $CO_2$ (20) is then directed toward a compression and transportation process for further processing. The liquid phase, containing less $CO_2$, and referred to as the lean absorption solution (17) is then pumped (E-14) to the mixing chamber (E-4).

By using the carbonate compounds in conjunction with carbonic anhydrase in the formulation, the rate of desorption is increased, the energy required for desorption may be reduced and more enzyme activity can be maintained for recycling back to the absorption unit.

Example 20

In another embodiment, the absorption solution rich in $CO_2$ without biocatalytic particles (15) is pumped (E-9) through a heat exchanger (E-10) where it is heated and then to the desorption column (E-11). In the desorption unit, the solution is further heated in order that the $CO_2$ is released from the solution in a gaseous state. Because of relatively high temperature used during desorption, water also vaporizes. Part of the absorption solution (18) is directed toward a reboiler (E-12) where it is heated to a temperature enabling $CO_2$ desorption. Gaseous $CO_2$ together with water vapour are cooled down, water condenses and is fed back to the desorption unit (19). Dry gaseous $CO_2$ (20) is then directed toward a compression and transportation process for further processing. The liquid phase, containing less $CO_2$, and referred to as the lean absorption solution (17) is then pumped (E-14) to the heat exchanger (E-10) to be cooled down and fed to the mixing chamber (E-4). The temperature of the lean absorption solution (17) should be low enough not to denature the enzyme.

Example 21

In one embodiment, in addition to carbonate compounds there may also be amino acids used in the absorption solution. The amino acids may include potassium salt of amino acids. The amino acids may be for instance glycine, proline, arginine, histidine, lysine, aspartic acid, glutamic acid, methionine, serine, threonine, glutamine, cysteine, asparagine, valine, leucine, isoleucine, alanine, valine, tyrosine, tryptophan, phenylalanine, and derivatives such as taurine, N,cyclohexyl 1,3-propanediamine, N-secondary butyl glycine, N-methyl N-secondary butyl glycine, diethylglycine, dimethylglycine, sarcosine, methyl taurine, methyl-α-aminopropionic acid, N-(β-ethoxy)taurine, N-(β-aminoethyl)taurine, N-methyl alanine, 6-aminohexanoic acid. In this case the amino acid may act as an absorption promoter to further increase the performance of the formulation, process and system. In one preferred embodiment, the amino acid promoter is used in conjunction with the biocatalyst immobilised on a packing in a packed-tower absorption reactor.

It should also be noted that the absorption and desorption reactors may be various different types depending on the particular process to be performed. The reactors types may be chosen depending on the presence of free-flowing biocatalysts or micro-particles with immobilised biocatalysts, the degree of precipitation of carbonate species, pressure, temperature, flue gas conditions and properties, etc. The absorption reactor, for example, may be a packed-tower, vertical or horizontal spray scrubber, or fluidised bed reactor.

Example 22

In the case that enzymes are free flowing in the absorption solution and are robust to desorption operating conditions, the process may be slightly different from the one shown in FIG. 1. For such a case, units E-3, E-6 and E-9 may not be present since they are required for the processing of the biocatalytic particles in the absorption solution. Unit E-4 would be used to introduce new enzyme in the process.

Example 23

An experiment was conducted in an absorption packed column. The absorption solution is an aqueous solution of potassium carbonate ($K_2CO_3$) 1.45 M. This absorption solution is contacted counter-currently with a gas phase with a $CO_2$ concentration of 130,000 ppm. Liquid flow rate was 0.60 g/min and gas flow rate was 60 g/min corresponding to L/G of 10 (g/g). Gas and absorption solution were at room temperature. Operating pressure of the absorber was set at 1.4 psig. The column has a 7.5 cm diameter and a 50 cm height. Packing material is polymeric Raschig rings 0.25 inch. Two tests were performed: the first with no activator, the second with CLEAs containing 26% (w/w) of the 5X enzyme (non optimised immobilization protocol). Particle size ranged between 4-9 μm. The enzyme concentration in the absorption solution was 0.1 g/L.

The results obtained showed that $CO_2$ transfer rate was increased by a factor of 2.7 as the $CO_2$ removal rate went from 11 to 30 mmol/min with the CLEAs.

Example 24

This example provides data to demonstrate that enzyme immobilization increases enzyme stability. Data are shown for enzyme immobilized on nylon micro-particles. To evaluate the impact of immobilization on enzyme stability, the stability of immobilized enzymes was evaluated and compared to the stability of the same enzyme in a soluble form.

Figure 7:
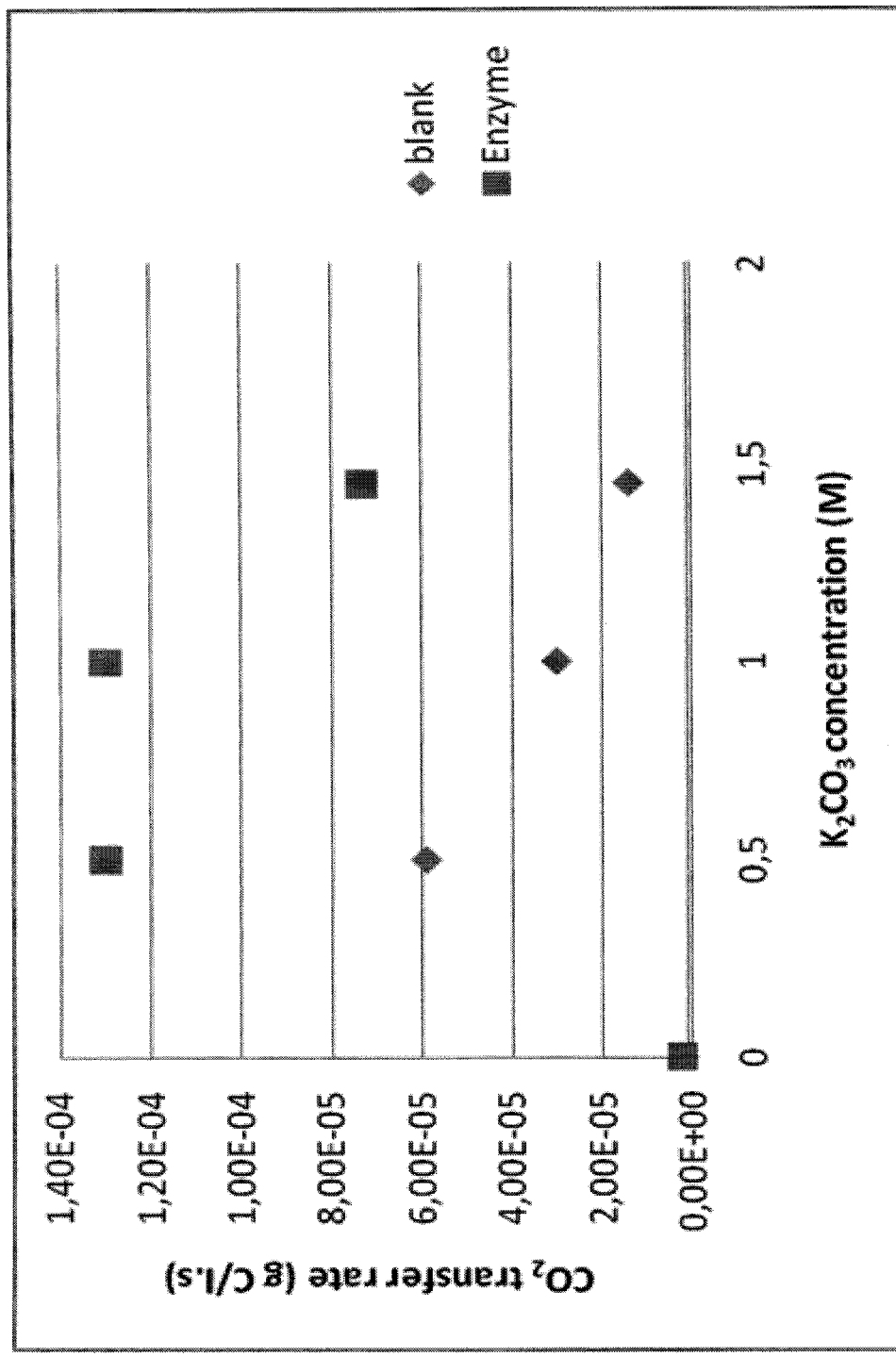
FIG. 7 is a graph of $CO_2$ transfer rate in $K_2CO_3$ solutions in the presence of 0.5 g/L of carbonic anhydrase at a temperature of 20° C.

Non-limiting example of nylon micro-particles:

Micro-particles were prepared through the following non-optimized steps:

Surface treatment of nylon micro-particles with glutaraldehyde
Addition of polyethyleneimine
Addition of glutaraldehyde
Enzyme fixation (human carbonic anhydrase type II)
Aldehyde group blocking with polyethyleneimine Following immobilization, the enzyme micro-particles and soluble enzyme were exposed to MDEA 2M at 40° C. At specific exposure times, samples were withdrawn and activity was measured. Results are expressed as residual activity, which is the ratio of the activity of the enzyme at a given exposure time t to the enzyme activity at time 0. FIG. 7 illustrates the results.

Figure 8:
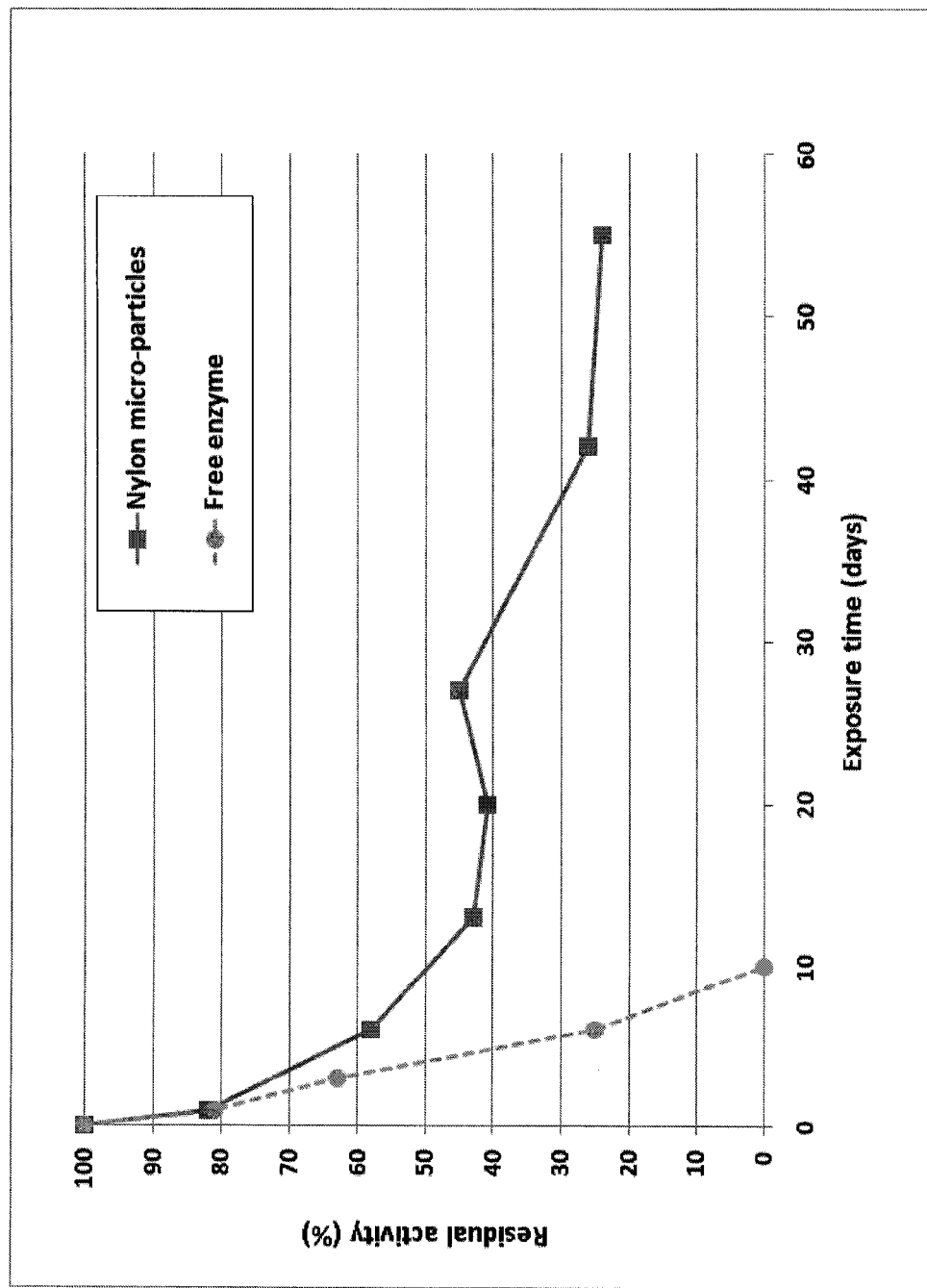
FIG. 8 is a graph showing evolution of residual activity of enzyme micro-particles exposed to MDEA 2M at 40° C., illustrating stability effect.

Results show that free enzyme loses all activity with 10 days, whereas micro-particles still retain 40% residual activity after 56 days. From this result, it is clear that immobilization increases enzyme stability under these conditions. FIG. 8 illustrates the results. In optional aspects of the present invention, the biocatalyst is provided to enable increased stability around or above the stability increase illustrated in the examples.

These results show the potential of immobilization to increase the stability of carbonic anhydrase at higher temperature conditions that are found in a $CO_2$ capture process. These results were obtained in MDEA 2M at 40° C. and it is expected that a similar increase in stability will also be present in carbonate solutions. In optional aspects of the present invention, the biocatalyst is provided to enable increased stability around or above the stability increase illustrated in the examples.

It should also be noted that the absorption and desorption units that may be used with embodiments of the present invention can be different types depending on various parameters and operating conditions. The reactors types may be chosen depending on the presence of free biocatalysts, biocatalytic micro-particles, biocatalytic fixed packing, etc. The units may be, for example, in the form of a packed reactor, spray reactor, fluidised bed reactor, etc., may have various configurations such as vertical, horizontal, etc., and the overall system may use multiple units in parallel or in series, as the case may be.

It should be understood that the aspects and embodiments described and illustrated herein do not restrict what has actually been invented.

The invention claimed is:

1. A process for capturing $CO_2$ from a $CO_2$-containing gas comprising:

contacting the $CO_2$-containing gas with an absorption mixture comprising water, carbonic anhydrase and a carbonate compound to enable dissolution and transformation of $CO_2$ into bicarbonate and hydrogen ions, thereby producing a $CO_2$-depleted gas and an ion-rich solution, the carbonate compound being selected and used in a sufficient amount in the absorption mixture such that the ion-rich solution contains bicarbonate precipitates; and subjecting the ion-rich solution to desorption wherein the carbonate compound promotes release of the bicarbonate ions from the ion-rich solution producing a $CO_2$ gas stream and an ion-depleted solution.

2. The process of claim 1, comprising removing the carbonic anhydrase from the ion-rich solution prior to subjecting the ion-rich solution to the desorption.

3. The process of claim 1, comprising removing the carbonic anhydrase from the ion-rich solution after subjecting the ion-rich solution to the desorption.

4. The process of claim 2, comprising recycling the ion-lean solution to form at least a part of the absorption mixture for re-contacting the $CO_2$-containing gas.

5. The process of claim 2, comprising adding an amount of carbonic anhydrase into the ion-depleted solution to convert the solution into at least part of the absorption mixture for recycling to contact the $CO_2$-containing gas.

6. The process of claim 1, comprising removing the bicarbonate precipitates from the absorption mixture prior to subjecting the ion-rich solution to the desorption.

7. The process of claim 1, wherein the bicarbonate precipitates remain in the ion-rich solution upon subjecting the ion-rich solution to the desorption, thereby converting into part of the $CO_2$ gas stream.

8. The process of claim 1, wherein the bicarbonate precipitates are composed of bicarbonate species comprising potassium bicarbonate, sodium bicarbonate, ammonium bicarbonate, or a mixture thereof.

9. The process of claim 1, wherein the carbonate compound comprises potassium carbonate, sodium carbonate or ammonium carbonate, or a combination thereof.

10. The process of claim 1, wherein the absorption mixture comprises an additional absorption compound, comprising piperidine, piperazine and derivatives thereof which are substituted by at least one alkanol group, alkanolamines, monoethanolamine (MEA), 2-amino-2-methyl-1-propanol (AMP), 2-(2-aminoethylamino)ethanol (AEE), 2-amino-2-hydroxymethyl-1,3-propanediol (Tris), amino acids, potassium or sodium salts of amino acids, glycine, proline, arginine, histidine, lysine, aspartic acid, glutamic acid, methionine, serine, threonine, glutamine, cysteine, asparagine, leucine, isoleucine, alanine, tyrosine, tryptophan, phenylalanine, and derivatives, taurine, N,cyclohexyl 1,3-propanediamine, N-secondary butyl glycine, N-methyl N-secondary butyl glycine, diethylglycine, dimethylglycine, sarcosine, methyl taurine, methyl-α-aminopropionic acid, N-(β-ethoxy)taurine, N-(β-aminoethy)taurine, N-methyl alanine, 6-aminohexanoic acid, or a combination thereof.

11. The process of claim 1, wherein contacting the absorption mixture with the $CO_2$-containing gas is performed in an absorption stage comprising at least one reactor selected from a packed tower, a vertical or horizontal spray scrubber, a fluidized bed reactor or a series of reactors comprising the same.

12. The process of claim 1, wherein a sufficient level of $CO_2$ loading is provided when producing the ion-rich solution to promote the precipitation of bicarbonate precipitates.

13. The process of claim 1, wherein the carbonate compound and carbonic anhydrase are provided in concentrations to achieve a maximum range of relative $CO_2$ transfer rate, with respect to a $CO_2$ transfer rate without carbonic anhydrase.

14. The process of claim 1, wherein the carbonate compound is provided in the absorption mixture in a concentration of at least about 0.1 M.

15. The process of claim 1, wherein the carbonate compound is provided in the absorption mixture in a concentration at or below saturation thereof.

16. The process of claim 1, wherein the carbonate compound comprises potassium carbonate and is provided in the absorption mixture in a concentration up to the solubility limit at a temperature range between about 40° C. and about 70° C.

17. The process of claim 1, wherein the carbonate compound comprises ammonium carbonate and is provided in the absorption mixture in a concentration up to the solubility limit at a temperature range between about 10° C. and about 70° C.

18. The process of claim 1, wherein the carbonate compound comprises sodium carbonate and is provided in the absorption mixture in a concentration up to the solubility limit at a temperature range between about 40° C. and about 70° C.

19. The process of claim 1, wherein the carbonic anhydrase is provided free in the water; dissolved in the water; immobilized on the surface of supports that are mixed in the water and are flowable therewith; entrapped or immobilized by or in porous supports that are mixed in the water and are flowable therewith; as cross-linked aggregates or crystals; or a combination thereof.

20. The process of claim 1, wherein the carbonic anhydrase is supported by micro-particles that are carried with the water.

* * * * *